United States Patent
Borgman et al.

(10) Patent No.: US 9,211,286 B2
(45) Date of Patent: Dec. 15, 2015

(54) TERCONAZOLE COMPOSITION AND METHOD

(75) Inventors: Robert J. Borgman, Mundelein, IL (US); James E. Juul, Wauconda, IL (US)

(73) Assignee: Curatek Pharmaceuticals Holding, Inc., Elk Grove Village, IL (US)

( * ) Notice: Subject to any disclaimer, the term of this patent is extended or adjusted under 35 U.S.C. 154(b) by 1752 days.

(21) Appl. No.: 11/519,303

(22) Filed: Sep. 12, 2006

(65) Prior Publication Data

US 2008/0063669 A1    Mar. 13, 2008

(51) Int. Cl.
- A61K 31/497 (2006.01)
- A61K 31/4196 (2006.01)
- A61K 9/00 (2006.01)
- A61K 47/38 (2006.01)
- A61K 31/357 (2006.01)

(52) U.S. Cl.
CPC ........... *A61K 31/4196* (2013.01); *A61K 9/0014* (2013.01); *A61K 9/0036* (2013.01); *A61K 47/38* (2013.01); *A61K 31/357* (2013.01)

(58) Field of Classification Search
CPC ........................ A61K 31/4196; A61K 31/357
USPC ......................................... 514/254.01, 254.07
See application file for complete search history.

(56) References Cited

U.S. PATENT DOCUMENTS

| | | | | |
|---|---|---|---|---|
| 4,861,580 A | * | 8/1989 | Janoff et al. | 424/1.21 |
| 2003/0130225 A1 | * | 7/2003 | Ahmad et al. | 514/45 |
| 2004/0019211 A1 | * | 1/2004 | Remenar et al. | 544/370 |
| 2004/0063722 A1 | * | 4/2004 | Whitefield et al. | 514/254.07 |

FOREIGN PATENT DOCUMENTS

| | | | | |
|---|---|---|---|---|
| GB | 2365770 B | * 7/2002 | | A61K 31/415 |
| GB | WO-2005/087270 | * 9/2005 | | A61K 45/06 |
| WO | WO-03/092650 A1 | * 11/2003 | | A61K 9/00 |

OTHER PUBLICATIONS

Sood, G., Terconazole Cream for Non-Candida albicans Fungal Vaginitis: Results of a Retrospective Analysis, Infectious Diseases in Obstetrics and Gynecology, 2000 Wiley-Liss, Inc., 8:240-243.*

* cited by examiner

*Primary Examiner* — Rebecca Prouty
*Assistant Examiner* — Danielle Sullivan
(74) *Attorney, Agent, or Firm* — Olson & Cepuritis, Ltd.

(57) ABSTRACT

An aqueous terconazole composition comprises at least about 0.4 percent by weight of terconazole dissolved in water, and a terconazole crystallization-inhibiting amount of an organic acid. Preferably the organic acid is a water soluble alkyl carboxylic acid, a polybasic organic acid, or a combination thereof. The composition is free from terconazole crystals at an ambient temperature of about 20° C. Methods of preparing the composition are also described. The compositions provide for improved therapeutic release of terconazole.

6 Claims, 1 Drawing Sheet

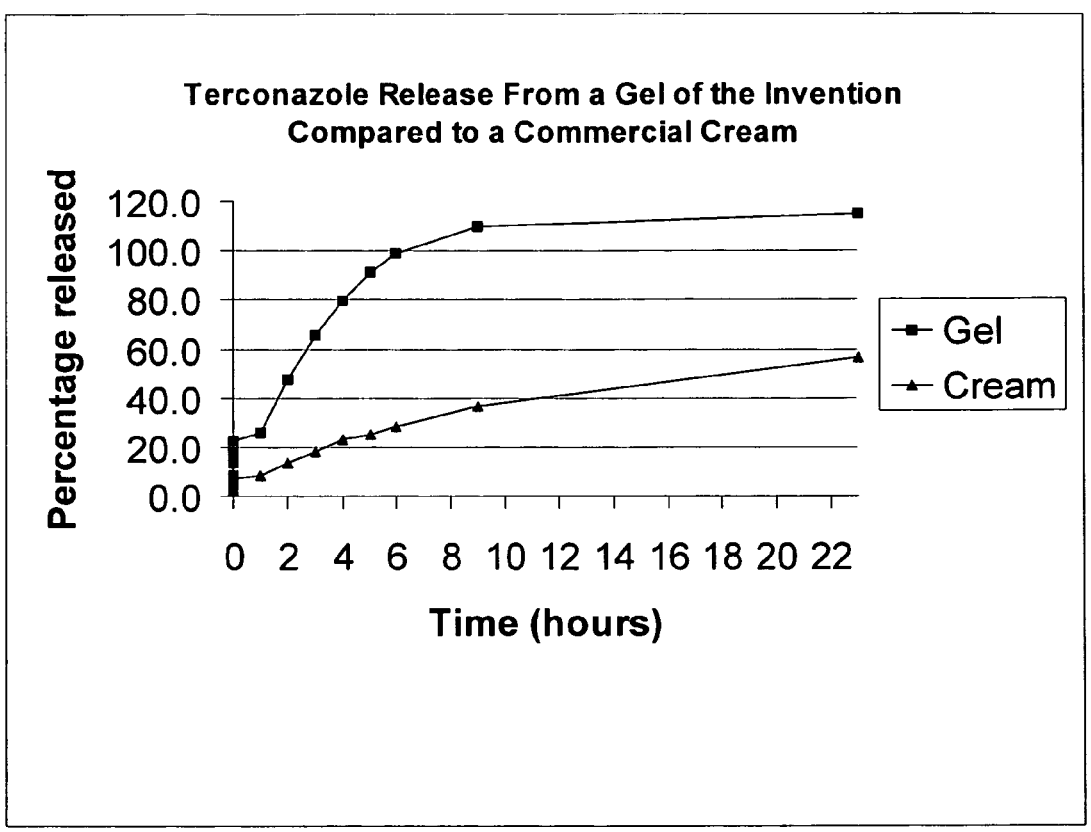

TERCONAZOLE COMPOSITION AND METHOD

FIELD OF THE INVENTION

The invention relates generally to compositions comprising terconazole, which are useful for treatment of microbiological infections. More particularly, the invention relates to aqueous solutions of terconazole and methods of preparing said solutions.

BACKGROUND OF THE INVENTION

Terconazole (cis-1-[p[[2-(2,4-dichlorophenyl)-2-(1H-1,2,4-triazol-1-ylmethyl)-1,3-dioxolan-4-yl]methoxy]phenyl]-4-isopropylpiperazine) ($C_{26}H_{31}Cl_2N_5O_3$) is a drug which has been useful for treatment of vaginal yeast infections as a cream containing about 0.4 or 0.8 percent by weight terconazole.

Terconazole is substantially insoluble in water at neutral pH. Terconazole hydrochloride has a solubility of about 0.007 percent by weight in water at neutral pH. Because of this low solubility, it is difficult to obtain stable terconazole solutions in water at concentrations required for therapeutic effect.

There is a need for aqueous terconazole solutions that include at least about 0.4 percent by weight dissolved terconazole, and which are free from terconazole crystals. Such solutions are useful in the preparation of pharmaceutical products for the treatment of yeast infections. Viscous aqueous compositions are particularly desirable, because they provide rapid release of the terconazole and generate the relatively high terconazole concentrations required for rapid killing of pathogens. The present invention provides such aqueous terconazole compositions.

SUMMARY OF THE INVENTION

An aqueous terconazole composition of the invention comprises at least about 0.4 percent by weight of terconazole dissolved in water, and a terconazole crystallization-inhibiting amount of an organic acid. The composition is free from terconazole crystals at an ambient temperature of about 20° C. Preferably, the organic acid is a water-soluble alkyl carboxylic acid (e.g., acetic acid), or a water-soluble polybasic organic acid (e.g., citric acid). The compositions are useful for treating vaginal yeast infections.

In a preferred embodiment, the composition includes at least about 0.8 percent by weight of terconazole dissolved in water. In other preferred embodiments, the solution comprises up to about 3 percent by weight of dissolved terconazole. Preferably, the organic acid is present in the composition in a molar amount in the range of about 50 to about 150 mole percent based on the molar amount of terconazole dissolved therein, more preferably at least equal to the molar amount of terconazole dissolved in the composition. Optionally, viscosity modifying agents, such as thickeners, can be included in the compositions of the invention to provide gels of other viscous products, which are particularly suitable for vaginal or topical application.

A method aspect of the present invention involves preparing an aqueous solution of terconazole comprising at least about 0.4 percent by weight of terconazole dissolved in water. The method comprises dissolving terconazole in water containing a terconazole crystallization-inhibiting amount of an organic acid.

BRIEF DESCRIPTION OF THE DRAWINGS

FIG. 1 depicts a graph of terconazole release versus time for a gel composition of the invention containing dissolved terconazole (labeled "Gel") compared to a commercial terconazole cream (labeled "Cream").

DETAILED DESCRIPTION OF PREFERRED EMBODIMENTS

The terms "pharmaceutically acceptable", "physiologically tolerable", "physiologically compatible", and grammatical variations thereof, as used herein and in the appended claims as they refer to electrolytes (e.g., salts), bases, diluents, preservatives, buffers and other excipients, are used interchangeably and represent that the materials are capable of topical administration to human skin and to the human vagina without the production of medically unacceptable levels of undesirable physiological effects such as irritation, itching, stinging, or systemic effects such as nausea, dizziness, and the like.

The present invention provides aqueous terconazole solutions having a concentration of dissolved terconazole of at least about 0.4 percent by weight, which are free from terconazole crystals. In the solutions of the present invention, terconazole is solubilized by the presence of a terconazole crystallization-inhibiting amount of an organic acid. The compositions preferably have an acidic pH value in the range of about 3.5 to about 6.

In some preferred embodiments the organic acid is a water-soluble alkyl carboxylic acid, such as acetic acid and the like. In other preferred embodiments the organic acid is a water-soluble polybasic organic acid, such as malic acid, citric acid, tartaric acid, a polyacrylic acid, and the like. In yet other preferred embodiments, the organic acid can be a mixture of one or more water-soluble alkyl carboxylic acids, a mixture of one or more polybasic organic acids, or a combination of one or more water-soluble alkyl carboxylic acid with one or more polybasic organic acids. The organic acid can also be a crosslinked polyacrylic acid, if desired. In a particularly preferred embodiment the organic acid comprises at least one acid selected from the group consisting of acetic acid, citric acid, tartaric acid, and malic acid.

Preferably, the organic acid is present in the composition at a concentration in the range of about 50 to about 150 mole percent based upon the molar amount of terconazole dissolved in the composition. More preferably, the organic acid preferably is present in the composition in a molar amount at least about equal to the molar amount of terconazole dissolved in the composition.

The compositions of the present invention optionally can include a physiologically tolerable preservative, as well as pharmaceutically acceptable excipients, so long as the optional components do not interfere with the solubility of the terconazole.

Suitable physiologically tolerable preservatives include bacteriostats, preservatives, inhibitors, and the like, such as methyl, ethyl, propyl, and butyl esters of parahydroxybenzoic acid (parabens); propyl gallate; sorbic acid and its sodium and potassium salts; propionic acid and its calcium and sodium salts; 6-acetoxy-2,4-dimethyl-m-dioxane; 2-bromo-2-nitropropane-1,3-diol; salicylanilides such as dibromosalicylanilide and tribromosalicylamilide, the cis isomer of 1-(3-chloroallyl)-3,5,7-triaza-1-azanidadamantane chloride; hexachlorophene; sodium benzoate; chelating agents such as ethylene diaminetetraacetic acid (EDTA), citric acid, and their alkali metal salts; phenolic compounds such as butyl hydroxyanisole, butylhydroxytoluene, chloro- and bromocresols, and the like; quaternary ammonium compounds such as benzalkonium chloride; aromatic alcohols such as 2-phenylethyl alcohol and benzyl alcohol; chlorobutanol; quinoline derivatives such as iodochlorohydroxyquinoline; and the like.

Pharmaceutically acceptable excipients that can be included in the compositions of the present invention include, for example, physiologically tolerable thickeners, surfactants, colorants, fragrances, water-soluble or water-miscible co-solvents, and the like, which are well known in the art. The compositions of the invention can be free-flowing solutions or gels.

Gelled compositions include a thickening agent, such as a hydroxypropyl methylcellulose (hypromellose) compound, a crosslinked polyacrylic acid, and the like. Examples of suitable crosslinked polyacrylic acids include CARBOPOL® thickening agents, and NOVEON® brand polycarbophil crosslinked polyacrylic acids, available from Noveon, Inc., Cleveland Ohio. A combination of two or more thickening agents can be utilized, as well. Crosslinked polyacrylic acids can also act as the organic acid to solubilize the terconazole.

The present invention also provides a method for preparing a solution comprising at least about 0.4 percent by weight of terconazole dissolved in water, free from terconazole crystals at an ambient temperature of about 20° C. The method comprises dissolving terconazole in an aqueous solution containing a terconazole crystallization-inhibiting amount of an organic acid as described hereinabove. Preferably, an amount of terconazole is dissolved in the solution to obtain a terconazole concentration of about 0.4 to about 0.8 percent by weight. In other preferred embodiments, the solution comprises up to about 3 percent by weight terconazole, based on the total weight of the composition. The concentration of organic acid in the solution preferably is at least about equal to the molar amount of terconazole dissolved in the solution.

Another aspect of the present invention is an article of manufacture comprising packaging material and at least one terconazole composition of the invention in at least one sealed container within the packaging material. Preferably, the compositions are gels containing a thickening agent. The container comprises a label that includes printed indicia describing the contents, such as a listing of ingredients, the manufacturer's name and address, and the like. Preferably, the packaging material also includes a printed insert including detailed information on the composition, its method of administration for treatment of infections, side effects, contraindications, and the like indicia, which may be required by governmental agencies responsible for regulation of pharmaceutical products. The articles of manufacture may also include applicators, such as a tubular applicator that can be used in conjunction with a storage vessel or a squeezable tube to aid in applying the compositions of the invention (e.g., into the vagina). In addition, the container can be a single use packet or a pre-filled applicator.

The following non-limiting examples further illustrate the present invention.

EXAMPLE 1

Solubilization of Terconazole in Water

Weighed amounts of terconazole were added to separate containers including an acid in water, and applying heat, if necessary, to dissolve the terconazole. The amount of acid was selected to be about equimolar with the amount of terconazole added. After the terconazole was dissolved, each solution was cooled to about 4° C. to force crystallization of some of the terconazole. If crystals were not observed upon cooling, seed crystals of terconazole were added, and the solutions were again cooled and maintained at about 4° C. to force crystallization of some of the terconazole. After allowing for crystal formation, the solutions were allowed to warm to room temperature (about 20° C.). Each solution was observed at about 20° C. over a period of about 14 days to determine if the crystals would re-dissolve. The absence of crystals after 14 days indicates that the acid salt of the terconazole is soluble at the concentration of the prepared solution. Table 1 includes dissolution data for a number of compositions comprising varying amounts of terconazole and various acids. The data in Table 1 clearly indicate that solutions having a terconazole concentration of at least about 3 percent by weight and free from terconazole crystals at 20° C. were obtained utilizing tartaric acid and malic acid.

TABLE 1

| Formulation | Presence or Absence of Crystals after 14 days at about 20° C. |
|---|---|
| Terconazole (1%) + hydrochloric acid | crystals |
| Terconazole (1%) + malic acid | no crystals |
| Terconazole (1%) + tartaric acid | no crystals |
| Terconazole (2%) + hydrochloric acid | crystals |
| Terconazole (2%) + malic acid | no crystals |
| Terconazole (2%) + tartaric acid | no crystals |
| Terconazole (3%) + hydrochloric acid | crystals |
| Terconazole (3%) + malic acid | no crystals |
| Terconazole (3%) + tartaric acid | no crystals |

In another experiment, the solubility of terconazole in water was increased to about 2.9 percent by weight using acetic acid at pH of about 5.

EXAMPLE 2

Terconazole Gel Composition

A terconazole gel composition containing citric acid was prepared from the components listed in Table 2. The gel was cooled to about 4° C. and seed crystals of terconazole were added in an attempt to force crystallization of some of the terconazole. No crystal formation was observed during this cooling and seeding period. The formulation was then observed at about 20° C. over a period of about 14 days to determine if terconazole crystals would form. No terconazole crystals formed during this period of time. These results clearly indicate that a gel composition having a terconazole concentration of about 2.4 percent by weight and free from terconazole crystals at 20° C. was obtained utilizing citric acid.

TABLE 2

| Ingredient | Percentage |
|---|---|
| Terconazole | 2.4 |
| MethoCel K100M | 2 |
| Propylene glycol | 5 |
| Methyl paraben | 0.08 |
| Propyl paraben | 0.02 |
| Citric acid | 0.3 |
| Sodium citrate | 0.15 |
| EDTA | 0.05 |
| Water | Q.S. to 100% |

In addition, a terconazole gel containing 0.8% by weight terconazole was prepared from the components listed in Table 3.

TABLE 3

| Ingredient | Percentage |
| --- | --- |
| Terconazole | 0.8 |
| MethoCel K100M | 2 |
| Propylene glycol | 5 |
| Methyl paraben | 0.08 |
| Propyl paraben | 0.02 |
| Citric acid | 0.3 |
| Sodium citrate | 0.15 |
| EDTA | 0.05 |
| Water | Q.S. to 100% |

The release of terconazole from this 0.8% gel was evaluated against a commercially available 0.8% terconazole cream. Approximately 0.5 g of each composition was placed in separate, previously wetted dialysis tubes, and the ends of the tubes were closed with plastic clips. Each dialysis tube was placed in a separate Petri dish containing about 20 mL of 1 millimolar citric acid in a 0.9 percent by weight sodium chloride solution adjusted to about pH 4.25. The Petri dish was then covered with a lid to eliminate evaporation. The Petri dishes were agitated with a magnetic stirrer and about 5 mL samples were withdrawn for assay at appropriate time intervals. The sample volume was replaced with an equal volume of blank medium (i.e., 0.9 percent saline with 1 mmol citric acid). The samples were assayed by UV spectroscopy at 230 nm (the wavelength maximum for terconazole) to determine the concentration of terconazole released from the compositions in the dialysis tubes. The concentration of terconazole in each sample was calculated using a calibration curve. Plots of the percentage of terconazole released over time for the gel composition of the invention and the commercial cream are shown in FIG. 1.

The 0.8% terconazole gel composition of the invention surprisingly released over 90% of the terconazole within five hours, and substantially all of the terconazole within 10 hours (see FIG. 1, upper curve). In contrast, the commercially available 0.8% terconazole cream released only about 25% of the terconazole within five hours and only about 57% of the terconazole within 23 hours (see FIG. 1, lower curve).

The compositions of the invention provide a significant improvement for the treatment of vaginal yeast infections, because they provide rapid and nearly complete release of the terconazole, compared to commercial products, which contained undissolved terconazole. The high levels of soluble terconazole provided by the compositions of the invention provide for rapid killing of pathogens.

Numerous variations and modifications of the embodiments described above may be effected without departing from the spirit and scope of the novel features of the invention. No limitations with respect to the specific embodiments illustrated herein are intended or should be inferred.

We claim:

1. An aqueous terconazole composition consisting of water; at least about 0.4 percent by weight and up to about 3 percent by weight of terconazole dissolved in the water; about 50 to about 150 mole percent of an organic acid based on the number of moles of terconazole dissolved in the composition; a physiologically tolerable preservative; and optionally one or more physiologically acceptable excipients selected from the group consisting of a thickener, a surfactant, a colorant, a fragrance, a water soluble co-solvent and a water miscible co-solvent;

the composition being free from terconazole crystals at an ambient temperature of about 20° C.; and wherein the organic acid is at least one acid selected from the group consisting of acetic acid, citric acid, tartaric acid, and malic acid.

2. The composition of claim 1 wherein the terconazole is present at a concentration of at least about 0.8 percent by weight.

3. The composition of claim 1 wherein the organic acid is present in the composition in a molar amount at least equal to the molar amount of terconazole dissolved in the composition.

4. The composition of claim 1 in which a thickening agent is present.

5. The composition of claim 4 wherein the thickening agent is a hydroxypropyl methylcellulose.

6. An article of manufacture for treating fungal infections comprising packaging material and at least one composition of claim 1 in at least one sealed container within the packaging material; the at least one container bearing a label that includes written indicia describing the contents thereof.

* * * * *